(12) United States Patent
Wang et al.

(10) Patent No.: US 9,322,213 B2
(45) Date of Patent: Apr. 26, 2016

(54) DISPLAY WITH AN ADJUSTABLE FOCUS MECHANISM

(71) Applicant: Delta Electronics, Inc., Taoyuan (TW)

(72) Inventors: Yeong-Feng Wang, Taoyuan (TW); Ming-Wei Tsai, Taoyuan (TW); Keh-Su Chang, Taoyuan (TW); Rong-Chang Liang, Cupertino, CA (US)

(73) Assignee: Delta Electronics, Inc., Taoyuan (TW)

( * ) Notice: Subject to any disclaimer, the term of this patent is extended or adjusted under 35 U.S.C. 154(b) by 0 days.

(21) Appl. No.: 14/657,843

(22) Filed: Mar. 13, 2015

(65) Prior Publication Data

US 2015/0185502 A1    Jul. 2, 2015

Related U.S. Application Data

(62) Division of application No. 13/590,465, filed on Aug. 21, 2012, now Pat. No. 9,006,642.

(51) Int. Cl.

| | |
|---|---|
| *G02B 27/00* | (2006.01) |
| *E06B 9/68* | (2006.01) |
| *A61B 3/103* | (2006.01) |
| *A61B 3/113* | (2006.01) |
| *G02C 7/08* | (2006.01) |
| *G02B 26/00* | (2006.01) |
| *G02F 1/29* | (2006.01) |

(52) U.S. Cl.
CPC . *E06B 9/68* (2013.01); *A61B 3/103* (2013.01); *A61B 3/113* (2013.01); *G02B 26/005* (2013.01); *G02C 7/08* (2013.01); *G02C 7/085* (2013.01); *E06B 2009/6827* (2013.01); *G02F 1/29* (2013.01)

(58) Field of Classification Search
CPC .............. G02B 2027/0178; G02B 2027/0187; G02B 7/0172; G02B 27/0118; A61B 3/103; A61B 3/113; G02C 7/085
See application file for complete search history.

(56) References Cited

U.S. PATENT DOCUMENTS

| | | | | |
|---|---|---|---|---|
| 5,644,324 | A * | 7/1997 | Maguire, Jr. | ....... G02B 27/2264 348/5 |
| 8,717,363 | B2 * | 5/2014 | Contractor | .............. G06F 3/013 345/419 |
| 2008/0194337 | A1 | 8/2008 | Hensel | |

\* cited by examiner

*Primary Examiner* — Tony Ko
(74) *Attorney, Agent, or Firm* — Muncy, Geissler, Olds & Lowe, P.C.

(57) ABSTRACT

An aspect of the invention provides a display with an adjustable focus mechanism. The display with an adjustable focus mechanism includes a display panel for emitting a plurality of rays to form an image; a light modulation device for receiving the rays from the display panel and adjusting an emergent angle of each ray; and a controller for providing a control signal to drive the light modulation device by estimating the emergent angle of the each of the rays according to an eyesight data of a user and a distance between the user and the display.

11 Claims, 8 Drawing Sheets

DISPLAY WITH AN ADJUSTABLE FOCUS MECHANISM

CROSS REFERENCE TO RELATED APPLICATIONS

This application is a Divisional of application Ser. No. 13/590,465, filed at Aug. 21 2012, the entirety of which is incorporated by reference herein.

BACKGROUND OF THE INVENTION

1. Field of the Invention

The present invention relates to a display with an adjustable focus mechanism.

2. Description of the Related Art

The visual system in humans allows individuals to assimilate information from the environment. The act of seeing starts when the lens of the eye focuses an image of its surroundings onto a light-sensitive membrane in the back of the eye, called the retina. The retina is actually part of the brain that is isolated to serve as a transducer for the conversion of patterns of light into neuronal signals. Then, the neuronal signals are processed by the brain and humans therefore see what they are seeing.

A refractive error, or refraction error, is an error in the focusing of light by the eye. The refractive error comprises different types, such as myopia, hyperopia or astigmatism. Myopia refers to a refractive defect of the optical properties of an eye that causes images to focus on a forward portion of the retina (i.e., a refractive error). Those optical defects are typically caused by, among other things, defects of the cornea, elongation of the eye structure, other conditions, or a combination of those conditions. Hyperopia, on the other hand, refers to a refractive error of the optical properties of an eye that causes images to focus on a portion behind the retina. Those optical defects are the result when the optics of the eye is not strong enough for the front to back length of the eye. Astigmatism refers to a refractive error that causes light entering the eye to focus on two points rather than one. It is caused by an uneven power of the cornea. Myopia, hyperopia, and astigmatism are the principle refractive errors that cause persons to seek treatment to correct their vision problems, but there is still no treatment that can deal with these problems at one time except for laser vision correction.

BRIEF SUMMARY OF THE INVENTION

An embodiment of the invention provides a focus adjustable apparatus adapted to be disposed on a transparent substrate to modulate a plurality of rays passing through the transparent substrate. The focus adjustable apparatus comprises a light modulation device, an eye tracking device, an eyesight status device and a controller. The light modulation device receives the rays from the transparent substrate and adjusts an emergent angle of each of the rays. The eye tracking device tracks a position of a user and estimates a distance between the user and the focus adjustable apparatus. The eyesight status device obtains an eyesight data of the user. The controller provides a control signal to drive the light modulation device by estimating the emergent angle of the each of the plurality of rays according to the distance between the user and the focus adjustable apparatus and the eyesight data of the user.

Another embodiment of the invention provides a display with an adjustable focus mechanism. The display comprises a display panel, a light modulation device and a controller. The display panel emits a plurality of rays to form an image. The light modulation device receives the rays from the display panel and adjusts an emergent angle of each ray. The controller provides a control signal to drive the light modulation device by estimating the emergent angle of the each of the plurality of rays according to an eyesight data of a user and a distance between the user and the display.

Another embodiment of the invention provides an electric curtain comprising sunlight detector and a light modulation device. The sunlight detector obtains a light data of sunlight. The light modulation device receives the sunlight and adjusts an emergent angle of the sunlight to refract the sunlight to a ceiling of a room.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
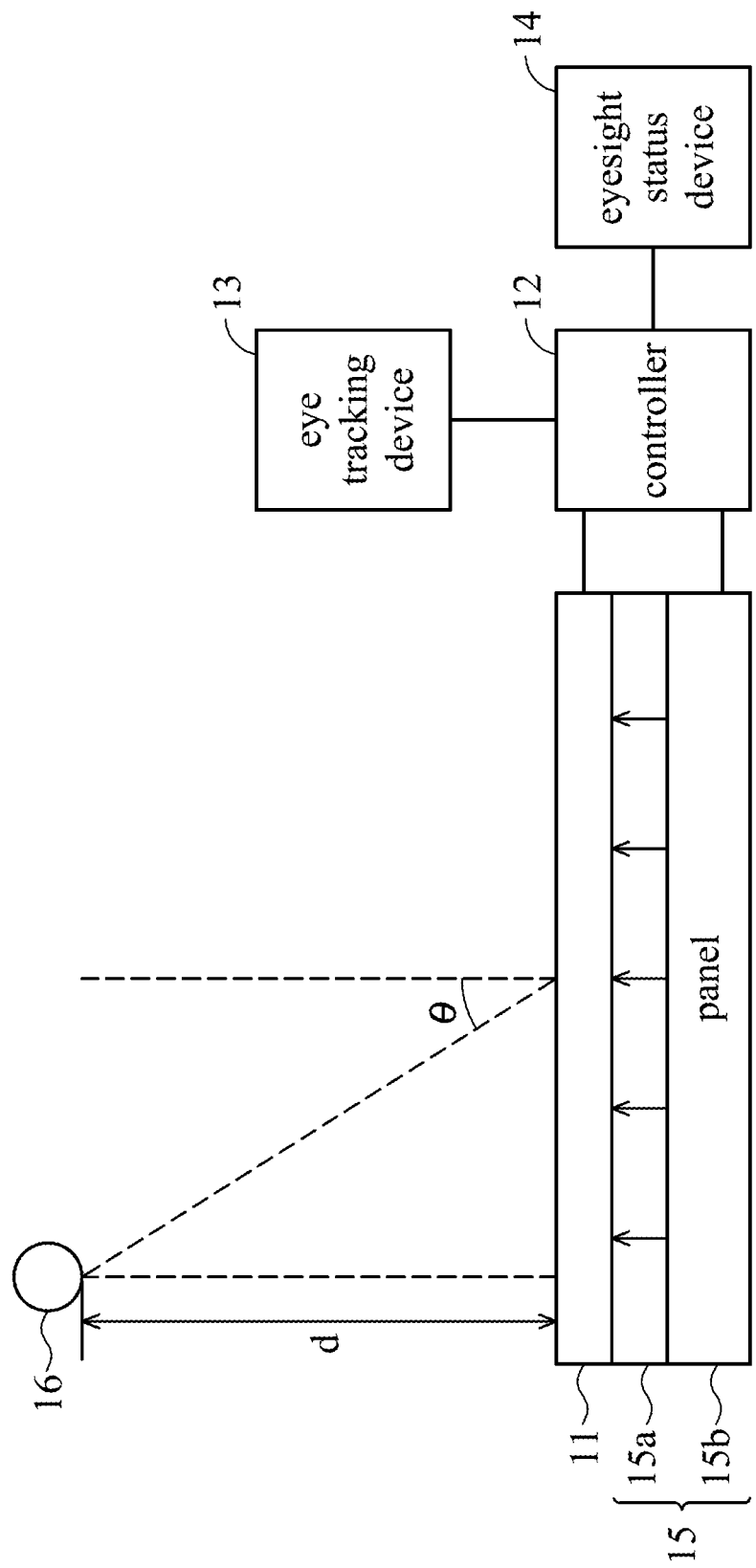
FIG. 1 is a schematic diagram of an embodiment of a focus adjustable apparatus according to the invention.

FIG. 1 is a schematic diagram of an embodiment of a focus adjustable apparatus according to the invention. The focus adjustable apparatus is disposed on a transparent substrate 15a of the display 15. The focus adjustable apparatus comprises a light modulation device 11, an eye tracking device 13, an eyesight status device 14 and a controller 12. The eye tracking device 13 tracks a position of a user 16 and estimates a distance d between the user 16 and the display 15. The eye tracking device 13 further estimates an angle θ that varies according to a relative position of the user 16 with reference to the light modulation device 11. The eyesight status device 14 obtains an eyesight data of the user. The eyesight data comprises an astigmatism degree, a degree of myopia or a degree of hyperopia of the user 16. The eyesight status device 14 may acquire the eyesight data of the user 16 from an electronic patient record database and the user 16 needs to provide some security authorization data to the eyesight status device 14, and then the eyesight status device 14 acquires the eyesight data according to the security authorization data. In another embodiment, the eyesight data is directly input to the eyesight status device 14 by the user. In another embodiment, the eyesight data is determined by an eye refractometer (not shown in FIG. 1). The eye refractometer is embedded in the eye tracking device. The eye refractometer projects a test pattern onto the retina of an eye to be examined, and determines the eyesight data according to the reflected test patter from the retina. Furthermore, the focus adjustable apparatus comprises a sensor for detecting an ambient light and the controller 12 controls the illumination of the rays refracted by the light modulation device 11 according to the illumination of the ambient light.

The light modulation device 11 receives a plurality of rays from the transparent substrate 15a and adjusts an emergent angle of each of the rays. The emergent angle is determined by the controller 12. The controller 12 estimate the emergent angle according to the eyesight data of the user 16 and the distance between the user 16 and the display 15. In one embodiment, the focus adjustable apparatus further comprises a calculator (not shown in FIG. 1) to receive the distance between the user 16 and the display 15 and the eyesight data of the user 16 to generate a control parameter, and then the controller 12 receives the control parameter and estimates the emergent angle according to the control parameter from the calculator. The rays refracted by the light modulation device 11 form an in-focus image on a retina of the user 16. In this embodiment, the light modulation device 11 comprises a plurality of electro-wetting units arranged in a matrix form. The electro-wetting units are driven by a dielectric force and the refraction index of each electro-wetting unit can be changed according to the magnitude of the dielectric force. In another embodiment, the light modulation device 11 is implemented by a plurality of Fresnel lens or Hologram elements arranged in a matrix or array form.

Figure 2:
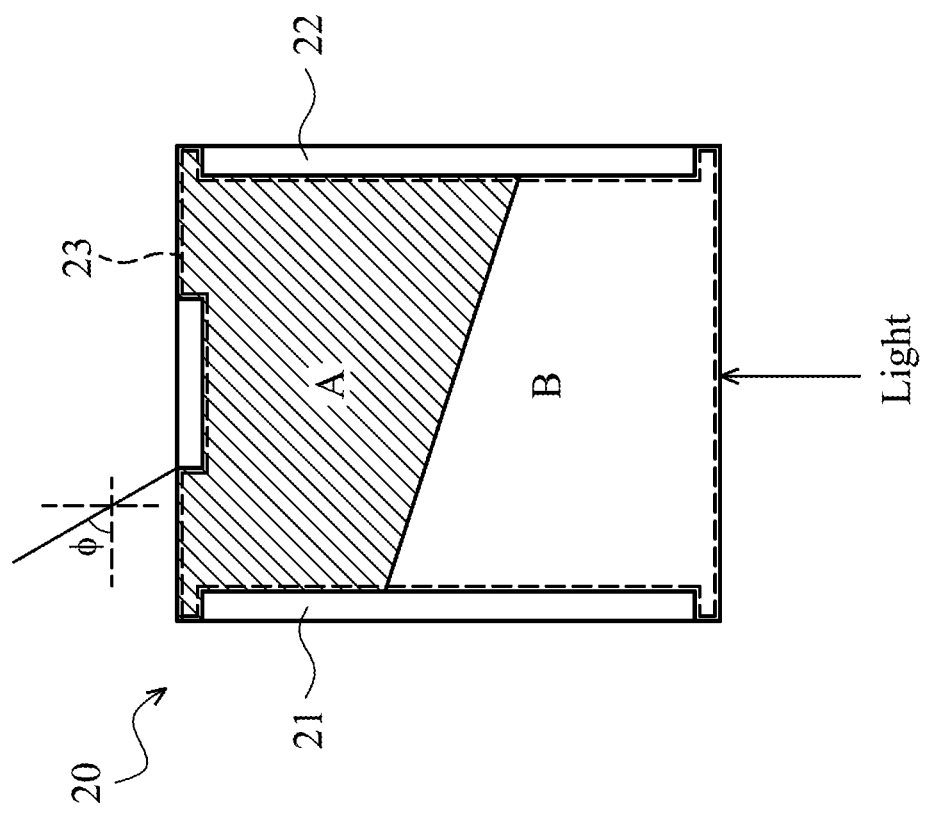
FIG. 2 is a schematic diagram of an electro-wetting unit according to an embodiment of the invention.

An electro-wetting unit is illustrated with FIG. 2. FIG. 2 is a schematic diagram of an electro-wetting unit according to an embodiment of the invention. The electro-wetting unit 20 comprises a first electrode 21, a second electrode 22, a compartment 23, and a first light modulating media (labeled as A) and a second light modulating media (labeled as B) filled in the compartment 23 (shown as the dotted line in FIG. 2), wherein the first light modulating media and second light modulating media are substantially immiscible and are of different refractive indices. The boundary between the first light and second light modulating media is adjusted by applying voltages to the first electrode 21 and the second electrode 22 according to a control signal from the controller, such as the controller 12 in FIG. 1. The control signal is determined according to the emergent angle θ by the controller.

Figure 3:
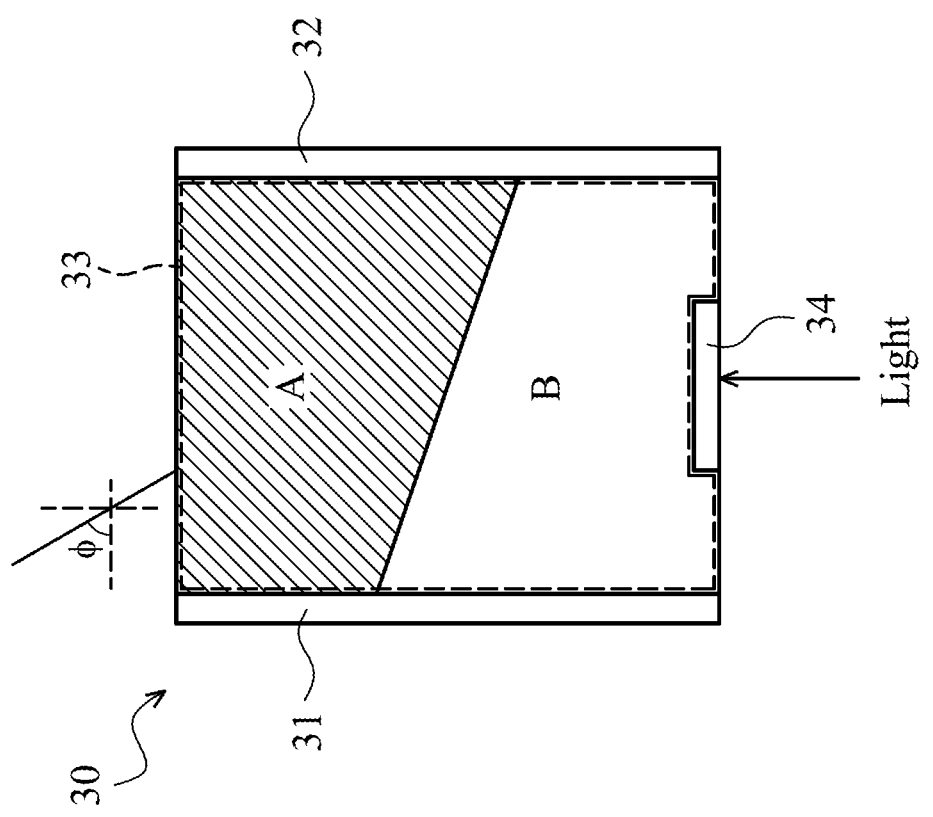
FIG. 3 is a schematic diagram of an electro-wetting unit according to another embodiment of the invention.

FIG. 3 is a schematic diagram of an electro-wetting unit according to another embodiment of the invention. The electro-wetting unit 30 comprises a first electrode 31, a second electrode 32, a compartment 33, a third electrode 34 and a first light modulating media (labeled as A) and a second light modulating media (labeled as B) filled in the compartment 33 (shown as the dotted line in FIG. 3), wherein the first light modulating media and second light modulating media are substantially immiscible and are of different refractive indices. In this embodiment, the first electrode 31, the second electrode 32 and the third electrode 34 are optically transparent electrodes. The boundary between the first light and second light modulating media is adjusted by applying voltages to the first electrode 31, the second electrode 32 and the third electrode 34 according to a control signal from the controller, such as the controller 12 in FIG. 1. The control signal is determined according to the emergent angle θ by the controller.

Figure 4:
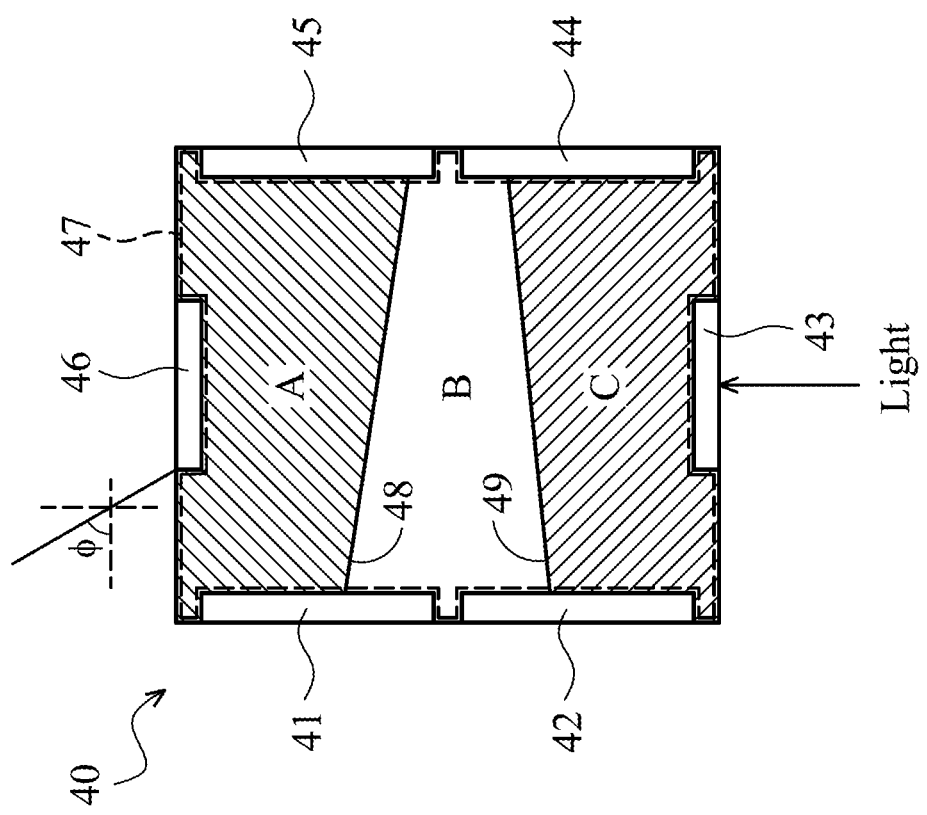
FIG. 4 is a schematic diagram of an electro-wetting unit according to another embodiment of the invention.

FIG. 4 is a schematic diagram of an electro-wetting unit according to another embodiment of the invention. The electro-wetting unit 40 comprises a first electrode 41, a second electrode 42, a bottom electrode 43, a third electrode 44, a fourth electrode 45, a upper electrode 46, a compartment 47, and a first light modulating media (labeled as A), a second light modulating media (labeled as B) and a third light modulating media (labeled as C) filled in the compartment 47 (shown as the dotted line in FIG. 4), wherein the first light modulating media, the second light modulating media and the third light modulating media are substantially immiscible and are of different refractive indices. In this embodiment, the first electrode 41, the second electrode 42, the bottom electrode 43, the third electrode 44, the fourth electrode 45 and the upper electrode 46 are optically transparent electrodes. The first boundary 48 and the second boundary 49 can be adjusted by applying voltages to the first electrode 41, the second electrode 42, the bottom electrode 43, the third electrode 44, the fourth electrode 45 and the upper electrode 46 according to a control signal from the controller, such as the controller 12 in FIG. 1. The control signal is determined according to the emergent angle θ by the controller. In other embodiments, the electro-wetting unit is named as an electronically switchable light modulating cell which is disclosed in a pending U.S. patent application Ser. No. 13/016,384, filed Jan. 28, 2011 and entitled "LIGHT MODULATING CELL, DEVICE AND SYSTEM", the entirety of which is incorporated by reference herein.

Figure 5:
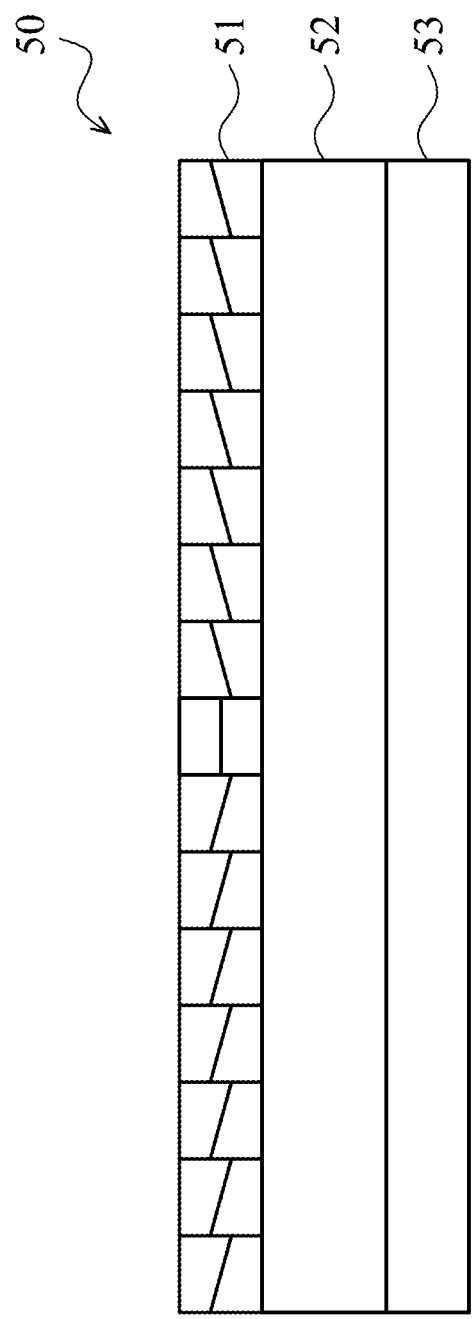
FIG. 5 is a cross section diagram of a light modulation device according to an embodiment of the invention.

FIG. 5 is a cross section diagram of a light modulation device according to an embodiment of the invention. The light modulation device 50 comprises a glue layer 53, a flexible substrate 52 and an electro-wetting array 51. The light modulation device 50 can be adhered to a display device, a plane glass, a window, a lampshade, an eyeglass or other transparent substance via the glue layer 53. The glue layer 53 may be implemented by a pressure sensitive adhesive material or a silica gel. The flexible substrate 52 may be a PET layer, a PI layer or a roll-able glass.

Figure 6:
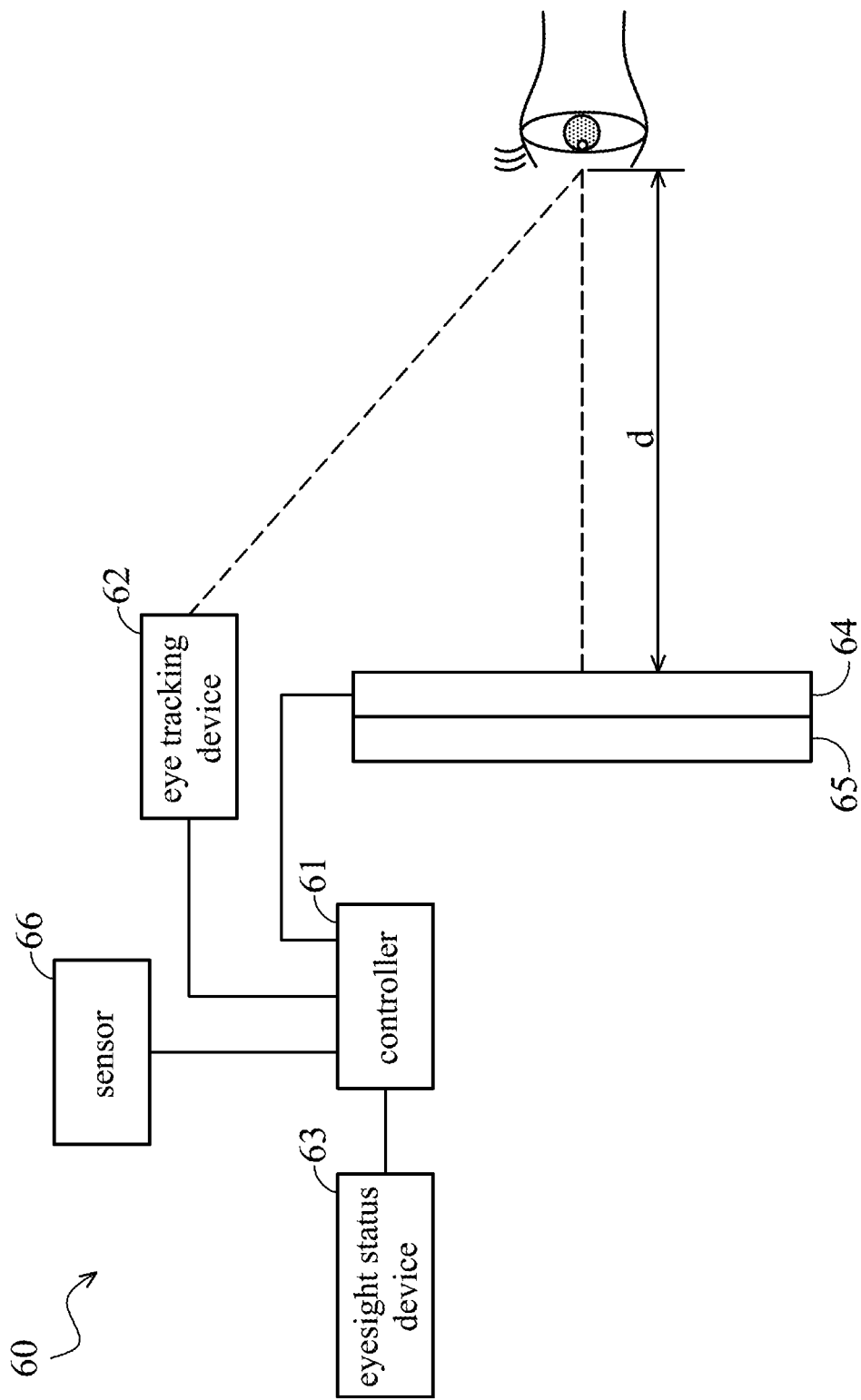
FIG. 6 is a schematic of an embodiment of a display device according to the invention.

FIG. 6 is a schematic of an embodiment of a display device according to the invention. The display device 60 comprises a controller 61, an eye tracking device 62, an eyesight status device 63, a light modulation device 64 and a panel 65. The light modulation device 64 is adhered to the panel 65. The eye tracking device 62 tracks a position of a user and estimates a distance d between the user and the display device 60. The eye tracking device 62 further estimates an angle θ that varies according to a relative position of the user with reference to the light modulation device 64. The eyesight status device 63 obtains an eyesight data of the user. The eyesight data may comprise an astigmatism degree, a degree of myopia or a degree of hyperopia of the user. The eyesight status device 63 may acquire the eyesight data of the user from an electronic patient record database and the user needs to provide some security authorization data to the eyesight status device 63, and then the eyesight status device 63 acquires the eyesight data according to the security authorization data. In another embodiment, the eyesight data is directly input to the eyesight status device 63 by the user. In another embodiment, the eyesight data is determined by an eye refractometer (not shown in FIG. 6) that is embedded in the eye tracking device 62. The eye refractometer projects a test pattern onto the retina of an eye to be examined, and determines the eyesight data according to the reflected test patter from the retina. The sensor 66 detects an ambient light and the controller 61 controls the illumination of the rays refracted by the light modulation device 64 according to the illumination of the ambient light.

The light modulation device 64 receives a plurality of rays from the panel 65 and adjusts an emergent angle of each ray. By adjusting the emergent angle of each ray, the image therefore can be correctly focused on the retina of the eyes of the user. The emergent angle is determined by the controller 61. The controller 61 estimates the emergent angle according to the eyesight data of the user and the distance between the user and the display 60. In one embodiment, the controller 61 comprises a calculator (not shown in FIG. 6). The calculator receives the distance between the user and the display 60 and the eyesight data of the user to generate a control parameter, and then the controller 61 receives the control parameter and estimates the emergent angle according to the control parameter from the calculator. The rays refracted by the light modulation device 64 form an in-focus image on a retina of the user. In this embodiment, the light modulation device 64 comprises a plurality of electro-wetting units arranged in a matrix form. The electro-wetting units are driven by a dielectric force and the refraction index of each electro-wetting unit can be changed according to the magnitude of the dielectric force. In another embodiment, the light modulation device 64 is implemented by a plurality of Fresnel lens or Hologram elements arranged in a matrix or array form. For examples of the electro-wetting unit, reference can be made to FIGS. 2-4.

In another embodiment, the user can directly control the light modulation device 64 via a remote control. The user can control emergent angles of rays refracted by the light modulation device 64 via the remote control. Once the emergent angles vary, the image seen by the user may be blurred or clear, thus, the user can instinctively control the light modulation device 64 only according to the displayed image. The control of the light modulation device 64 is similar to a zoom in/zoom out control or a focus control. Simply speaking, the light modulation device 64 plays a role similar to an eyeglass to ensure that the image can be correctly formed on the retina of the eyes of the user.

Figure 7:
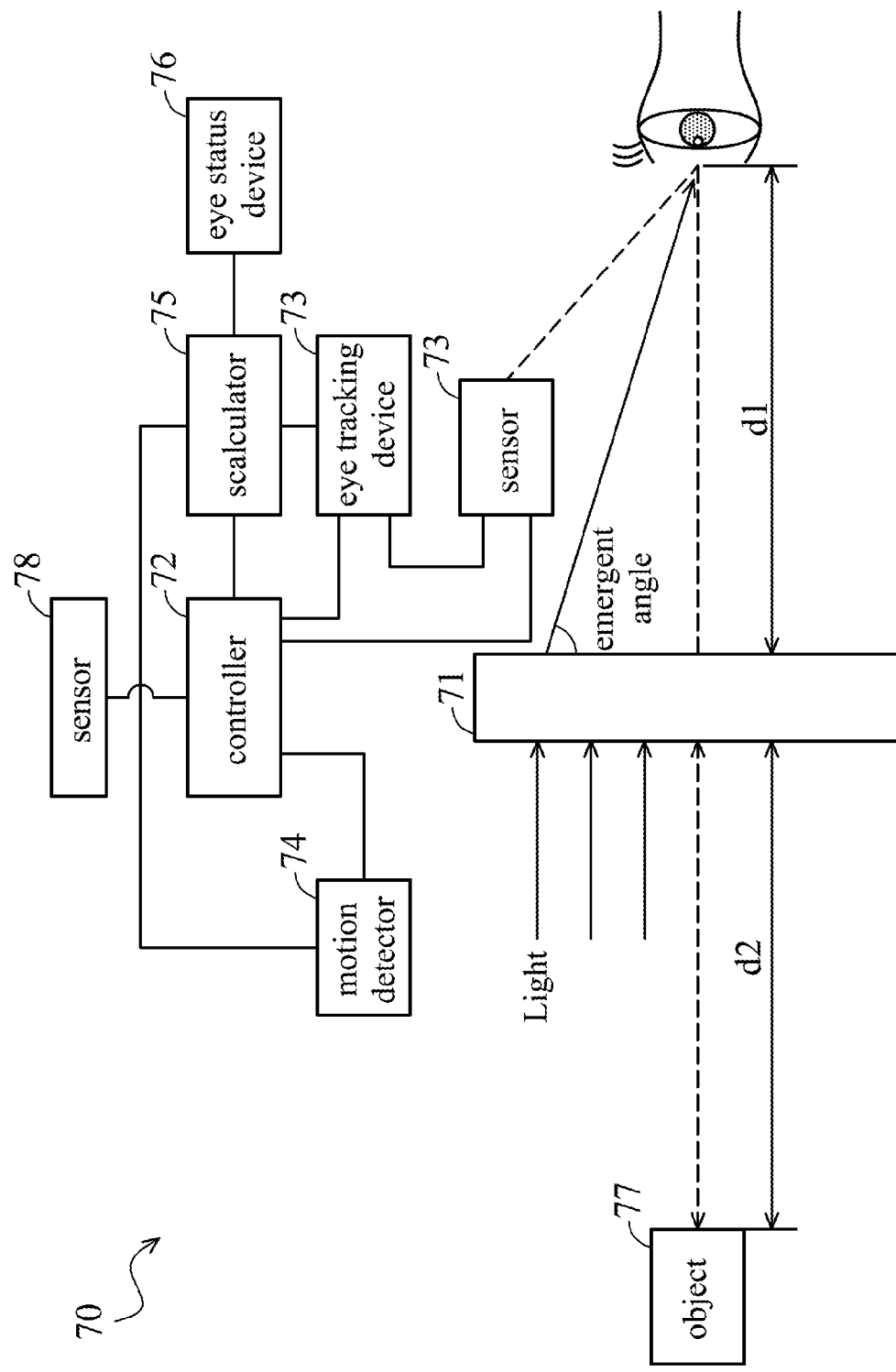
FIG. 7 is a schematic diagram of another embodiment of a focus adjustable apparatus according to the invention.

FIG. 7 is a schematic diagram of another embodiment of a focus adjustable apparatus according to the invention. The focus adjustable apparatus 70 comprises a light modulation device 71, a controller 72, an eye tracking device 73, a motion detector 74, a calculator 75 and an eye status device 76. The light modulation device 71 is adhered to an inner or outer surface of a windshield of a vehicle. For the detailed structure of the light modulation device 71, reference can be made to FIG. 5, and thus, is not described here for briefly. The eye tracking device 73 tracks a position of a user and estimates a first distance d1 between the user and the light modulation device 71 (or the windshield). The eye tracking device 73 further tracks the movement of the eyeball of a user and transmits an object information to the controller 72. The object information indicates which object, such as the object 77, the user is looking at. The object may be an obstacle, a moving vehicle or a moving/still object. The controller 72 then transmits a control signal to control the motion detector 74 to measure a second distance d2 between the object 77 and the light modulation device 71.

The eyesight status device 76 obtains eyesight data of the user. The eyesight data may comprise an astigmatism degree, a degree of myopia or a degree of hyperopia of the user. The eyesight status device 76 may acquire the eyesight data of the user from an electronic patient record database or a digital medical system and the user needs to provide some security authorization data to the eyesight status device 76 for acquiring the eyesight data. In another embodiment, the eyesight data is directly input to the eyesight status device 76 by the user. In another embodiment, the eyesight data is determined by an eye refractometer 77. The eye refractometer 77 projects a test pattern onto the retina of an eye to be examined, and determines the eyesight data according to the reflected test pattern? from the retina. The sensor 78 detects an ambient light and the controller 72 controls the illumination of the rays refracted by the light modulation device 71 according to the illumination of the ambient light. In this embodiment, the eye refractometer 77 and the sensor 78 are optional for the focus adjustable apparatus 70, but they still can be integrated into the focus adjustable apparatus 70.

The light modulation device 71 receives a plurality of rays from the object 77 and adjusts an emergent angle of each ray. By adjusting the emergent angle of each ray, the image of the object 77 therefore can be correctly focused on the retina of the eyes of the user. The emergent angle is determined by the controller 72. The controller 72 estimates the emergent angle according to the eyesight data of the user, the first distance d1 and the second distance d2. The calculator 75 receives the first distance, the second distance and the eyesight data of the user to generate a control parameter. Then, the controller 61 receives the control parameter to estimate the emergent angle accordingly. The rays refracted by the light modulation device 71 form an in-focus image on a retina of the user. In this embodiment, the light modulation device 71 comprises a plurality of electro-wetting units arranged in a matrix form. The electro-wetting units are driven by a dielectric force and the refraction index of each electro-wetting unit can be changed according to the magnitude of the dielectric force. In another embodiment, the light modulation device 71 is implemented by a plurality of Fresnel lens or Hologram elements arranged in a matrix or array form. For the examples of the electro-wetting unit, reference can be made to FIGS. 2-4, and thus, is not described here for briefly.

Figure 8:
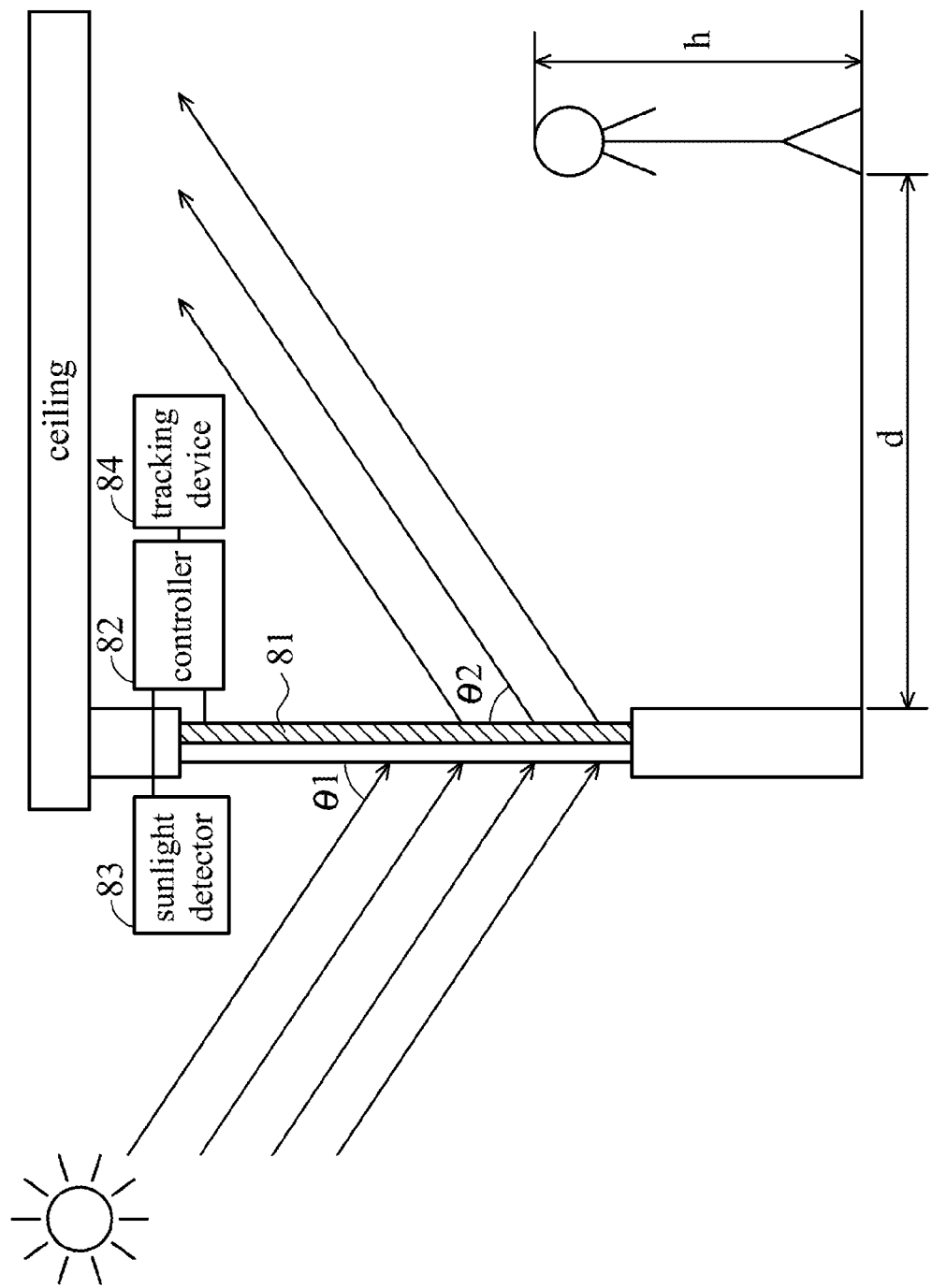
FIG. 8 is a schematic diagram of an embodiment of an electric curtain according to the invention.

FIG. 8 is a schematic diagram of an embodiment of an electric curtain according to the invention. The electric curtain comprises a light modulation device 81, a controller 82, sunlight detector 83 and a tracking device 84. The tracking device 84 tracks a position of the user and measures a distance d between the user and the light modulation device 81 and a height h of the user. The height can be input by the user via a remote control. The user can also control the angle $\theta_2$ via the remote control. The sunlight detector 83 obtains light information of sunlight, such as an incident angle $\theta_1$ and the illumination. The controller 82 then estimates the angle $\theta_2$ according to the incident angle $\theta_1$, the distance d and the height h. The light modulation device 81 receives a control signal from the controller to refract the sunlight to a ceiling of a room. In this embodiment, the controller 82 transmits a control signal to adjust the angle $\theta_2$ and the amount of the sunlight passing through the light modulation device 81. The light modulation device 81 is a flexible film and adheres to a window. For the detailed structure of the light modulation device 81, reference can be made to FIG. 5, and thus, is not described here for briefly.

Since the light modulation device 81 can refract the sunlight to the ceiling of the room, the user may not directly feel the heat from the sunlight and the temperature of the room can be regulated at a higher temperature by an air conditioner. Furthermore, the light modulation device 81 prevents the eye of a user from receiving direct sunlight.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A display with an adjustable focus mechanism, comprising:
    a display panel for emitting a plurality of rays to form an image;
    a light modulation device for receiving the rays from the display panel and adjusting an emergent angle of each ray; and
    a controller for providing a control signal to drive the light modulation device by estimating the emergent angle of the each of the rays according to an eyesight data of a user and a distance between the user and the display.

2. The display as claimed in claim 1, further comprising:
    an eyesight status device for obtaining the eyesight data of the user wherein the emergent angle of each of the plurality of rays is determined further according to the eyesight data of the user.

3. The display as claimed in claim 1, further comprising:
    an eye tracking device for tracking a position of the user and estimating the distance between the user and the display.

4. The display as claimed in claim 3, wherein the eye tracking device comprises an auto refractometer capable of automatically tracing eyes of the user and detecting the eyesight data of the user.

5. The display as claimed in claim 1, wherein the eyesight data comprises an astigmatism degree, a degree of myopia or a degree of hyperopia of the user.

6. The display as claimed in claim 1, wherein the eyesight data is directly input to the eyesight status device by the user or acquired from an electronic patient record database.

7. The display as claimed in claim 1, wherein the light modulation device comprises a plurality of electro-wetting units arranged in a matrix form.

8. The display as claimed in claim 7, wherein the plurality of electro-wetting units are driven by a dielectric force.

9. The display as claimed in claim 7, wherein each of the plurality of electro-wetting units comprises a first electrode, a second electrode, a compartment, and a first and second light modulating media filled in the compartment, wherein the first light and second light modulating media are substantially immiscible and are of different refractive indices, and a boundary between the first light and second light modulating media is adjusted by applying a voltage to the first and second electrodes according to the control signal from the controller.

10. The display as claimed in claim 3, further comprising a calculator capable of receiving the distance between the user and the display and the eyesight data of the user to generate a control parameter, wherein the controller is capable of estimating the emergent angle according to the control parameter from the calculator.

11. The display as claimed in claim 1, wherein the each of the plurality of rays form an in-focus image on a retina of the user after the plurality of rays are refracted by the light modulation device.

* * * * *